United States Patent [19]

Umemoto et al.

[11] Patent Number: 5,767,059

[45] Date of Patent: Jun. 16, 1998

[54] CLEANSER COMPOSITION COMPRISING AN ALKALI METAL SALT OF A SECONDARY AMIDE-TYPE N-ACYLAMINO ACID, AND ALKALI METAL SALT OF A HIGHER FATTY ACID, AND AN AMPHOTERIC SURFACTANT

[75] Inventors: Isao Umemoto; Yasushi Kajihara, both of Tokyo, Japan

[73] Assignee: Kao Corporation, Tokyo, Japan

[21] Appl. No.: 703,535

[22] Filed: Aug. 27, 1996

[30] Foreign Application Priority Data

Sep. 4, 1995 [JP] Japan .................... 7-248321

[51] Int. Cl.[6] .................... C11D 1/10; C11D 1/88; C11D 9/02; C11D 1/32
[52] U.S. Cl. .................... 510/490; 510/481; 510/433; 510/119; 510/129; 510/123; 510/130; 510/152; 510/155; 510/158; 510/159
[58] Field of Search .................... 510/119, 129, 510/123, 130, 152, 155, 158, 159, 481, 490, 433

[56] References Cited

U.S. PATENT DOCUMENTS

| 4,678,598 | 7/1987 | Ogino et al. ........... 252/174.17 |
| 4,931,216 | 6/1990 | Igarashi et al. ........... 252/547 |
| 5,009,813 | 4/1991 | Watanabe et al. ........... 252/545 |
| 5,529,712 | 6/1996 | Sano et al. ........... 252/108 |
| 5,540,853 | 7/1996 | Trinh et al. ........... 510/101 |
| 5,616,552 | 4/1997 | Yoshihara et al. ........... 510/490 |

FOREIGN PATENT DOCUMENTS 4-211607  8/1992  Japan .

*Primary Examiner*—Paul Lieberman
*Assistant Examiner*—Charles Borer
*Attorney, Agent, or Firm*—Oblon, Spivak, McClelland, Maier & Neustadt, P.C.

[57] ABSTRACT

The present invention provides a cleanser composition which is free from any thickener, contains surfactant(s) at such a concentration as not to irritate the skin or mucosa, can impart an appropriate consistency to the cleanser, exhibits excellent foaming, can be easily taken out from a container in use and gives a good feel in use.

The cleanser composition comprises the following components (A), (B) and (C):

(A) an alkali metal salt of a secondary amide-type N-acylamino acid represented by formula (1):

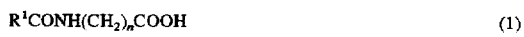

$$R^1CONH(CH_2)_nCOOH \qquad (1)$$

wherein $R^1CO$ represents a linear acyl group having 10 to 16 carbon atoms; and n is a number of 1 or 2;

(B) an alkali metal salt of a higher fatty acid; and (C) an amphoteric surfactant; and the mixing ratio by weight of (A+B)/C ranges from 2.5/1 to 1/2.

6 Claims, No Drawings

CLEANSER COMPOSITION COMPRISING AN ALKALI METAL SALT OF A SECONDARY AMIDE-TYPE N-ACYLAMINO ACID, AND ALKALI METAL SALT OF A HIGHER FATTY ACID, AND AN AMPHOTERIC SURFACTANT

FIELD OF THE INVENTION

This invention relates to a cleanser composition. More particularly, it relates to a cleanser composition which is very excellent in foaming power, can be easily taken out from a container and gives a good feel in use.

BACKGROUND OF THE INVENTION

Marketed liquid body cleansers are usually contained in plastic bottles, etc. Thus the commercial value of such a product largely depends on the easiness in taking out from the bottle, the texture in use and the post-use feel, in addition to the fundamental characteristics as a cleanser (little irritation to the skin and hair, excellent foaming power, sustained foaming, etc.).

In the conventional liquid body cleansers, therefore, attempts have been made to achieve an appropriate consistency in use by increasing the concentration of surfactants or to elevate the viscosity by adding polymeric thickeners such as cellulose derivatives, carboxyvinyl polymer, etc.

However, an increase in the surfactant concentration brings about some troubles, for example, irritation to the skin or mucosa in use, difficulties in rising. On the contrary, a decrease in the surfactant concentration results in a decrease in the viscosity. In such a case, the cleanser is taken out from the bottle in an unnecessarily large amount or gives a poor feel in use, which makes the product less convenience.

On the other hand, the addition of thickeners brings about troubles, for example, the thickeners are precipitated in some cases (depending on the types or concentrations of the surfactants or other additives or due to temperature change during storage or in use) to thereby make a transparent cleanser cloudy; the foam qualities to the surfactants are alerted; or the feel in use is seriously worsened.

SUMMARY OF THE INVENTION

An object of the present invention is to provide a cleanser composition having a high commercial value which contains surfactants at such a regulated concentration as to give no irritation to the skin or mucosa, has an appropriate consistency without using any thickener with a fear of lowering the commercial value of the cleanser as discussed above, and exhibits a high convenience in use and a good feel during and after cleansing, in addition to the fundamental characteristics as a cleanser (e.g., little irritation, excellent foaming power, sustained foaming, etc.).

To obtain a cleanser composition having these preferable properties, the present inventors have conducted extensive studies. As a result, they have found out that a cleanser composition having the desired properties can be unexpectedly obtained by combining specific surfactants at a specific mixing ratio, thus completing the present invention.

Accordingly, the present invention provides a cleanser composition comprising the following components (A), (B) and (C):

(A) an alkali metal salt of a secondary amide-type N-acylamino acid represented by formula (1):

$$R^1CONH(CH_2)_nCOOH \quad (1)$$

wherein $R^1CO$ represents a linear acyl group having 10 to 16 carbon atoms; and n is a number of 1 or 2;

(B) an alkali metal salt of a higher fatty acid; and
(C) an amphoteric surfactant;

wherein the mixing ratio by weight of (A+B)/C ranges from 2.5/1 to 1/2.

The components (A), (B) and (C) to be used in the cleanser composition of the present invention have been publicly well-known. It has been also known to use these components in combination (in JP-A-5-156282; the term "JP-A" as used herein means an "unexamined published Japanese patent application").

However, the present inventors have found out for the first time that the desired cleanser composition can be obtained by selecting the specific components (A), (B) and (C) from among these publicly well-known cleanser components and combining the components thus selected at a specific mixing ratio.

DETAILED DESCRIPTION OF THE INVENTION

Now, each of the components (A), (B) and (C) to be used in the cleanser composition of the present invention and the mixing ratio thereof will be described in detail. The secondary amide-type N-acylamino acid salt employed as the component (A) would react with calcium, etc. contained in tap water and thus form highly lubricating plate crystals. When contained in a cleanser composition, therefore, it imparts a good feel in use (post-use slipping property, etc.) to the product. The lubricating properties of the plate crystals formed by the reaction of the secondary amide-type N-acylamino acid salt with calcium may be determined by, for example, measuring the coefficient of static friction of the plate crystals on dry pig skin (Alloask, manufactured by Kotai Kasei Kogyo K.K.) reconstituted with physiological saline water. A sample showing the coefficient which is lower than the blank value (from the reconstituted state to the dry state) is regarded as good.

In the above-mentioned secondary amide-type N-acylamino acid salt, the linear acyl group represented by $R^1CO$ in the above formula (1) has from 10 to 16, preferably from 12 to 14, carbon atoms. Preferred examples thereof include caprinoyl, lauroyl and myristoyl groups. A linear acyl group having more than 16 carbon atoms is not preferable, since the lubricating properties of the plate crystals thus formed are deteriorated in this case. Also, it is not preferable that the linear acyl group has less than 10 carbon atoms, since the foaming power is deteriorated in this case. It is highly important that the above-mentioned secondary amide-type N-acylamino acid salt has the secondary amide structure wherein the N-acyl group is composed of the above-mentioned linear acyl. When the acyl group constituting the N-acyl group is a branched one or the amide has a tertiary amide structure, the formation of plate crystals is depressed or the crystals thus formed are not lubricative but sticky. Thus any desirable texture can be hardly obtained in such a case. A sodium salt of a secondary amide-type N-acylamino acid of the formula (1) wherein n is 2 has a high Krafft point and a low solubility in water, which makes it not so suitable for liquid cleansers.

Either one of these secondary amide-type N-acylamino acid salts or a mixture of two or more of the same may be used. It is not always necessary to add it in the form of a secondary amide-type N-acylamino acid salt. Namely, a secondary amide-type N-acylamino acid and a base may be independently added so as to form a secondary amide-type N-acylamino acid salt in the formulation system.

As the alkali metal salt of a higher fatty acid to be employed as the component (B) in the present invention, use can be made of salts of fatty acids having preferably from 8 to 22, more preferably from 12 to 18, carbon atoms. Preferred examples thereof include salts of a single fatty acid (e.g., lauric acid, myristic acid, palmitic acid, isostearic acid, oleic acid, etc.) and salts of mixed fatty acids (e.g., coconut oil fatty acids, beef tallow fatty acids, etc.).

It is not appropriate to use metal salts other than alkali metal salts, which are poor in solubility. On the other hand, use of basic salts other than metal salts (e.g., triethanolamine salts, etc.) brings about some disadvantages such that the product gradually becomes yellow due to prolonged heating in the production process; yellowing with the passage of storage time largely deteriorates the commercial value of the product; the feel in use is also worsened; etc. Therefore, it is necessary to use an alkali metal salt as the higher fatty acid salt and sodium, potassium or lithium salts are particularly preferable therefor.

Either one of these alkali metal salts of higher fatty acids or a mixture of two or more of the same may be used. It is not always necessary to add it in the form of a fatty acid salt. Namely, a fatty acid and a base may be independently added so as to form a fatty acid salt in the formulation system.

As the ampholytic surfactant to be employed as the component (C) in the present invention, it is preferable to use a betaine surfactant represented by the following formula (2):

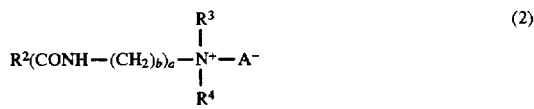

wherein $R^2$ represents a linear or branched alkyl or alkenyl group having from 9 to 22 carbon atoms; $R^3$ and $R^4$ are the same or different and each represents a linear or branched alkyl or hydroxyalkyl group having from 1 to 4 carbon atoms or —$(CH_2CH_2O)_cH$ (wherein c is a number of from 1 to 3); A represents —$CH_2CH(OH)CH_3SO_3$, —$(CH_2)_eSO_3$ or —$(CH_2)_eCOO$ (wherein d is an integer of from 2 to 5; and e is an integer of from 1 to 3); a is 0 or 1; and b is an integer of from 1 to 4.

Examples of the alkyl or alkenyl group having from 9 to 22 carbon atoms represented by $R^2$ in the above formula (2) include lauryl group, myristyl group, palmityl group, stearyl group, oleyl group, etc., and coconut oil alkyl group, palm oil alkyl group, beef tallow alkyl group, etc. Among these groups, alkyl groups having from 9 to 18 carbon atoms are preferable and lauryl, myristyl, stearyl and coconut oil alkyl groups are still preferable.

Examples of the alkyl group having 1 to 4 carbon atoms represented by $R^3$ and $R^4$ in the above formula (2) include methyl group, ethyl group, n-propyl group, isopropyl group, n-butyl group, tert-butyl group, hydroxyethyl group, etc. It is particularly preferable that $R^3$ and $R^4$ are both methyl groups.

Preferable examples of A include —$CH_2CH(OH)$ $CH_3SO_3$, —$CH_2COO$ and —$(CH_2)_3COO$.

Preferable examples of the component (C) include betaine coconut oil-alkyldimethylaminoacetate, betaine coconut oil fatty acid amidopropyldimethylaminoacetate, betaine stearyldihydroxyethylaminoacetate, laurylhydroxysulfobetaine, laurylsulfobetaine, etc. It is particularly preferable to use a hydroxysulfobetaine surfactant as the component (C), since the desired characteristics of the cleanser composition of the present invention can be distinctly established thereby. Either one of these amphoteric surfactants or a mixture of two or more thereof may be used as the component (C).

A particularly preferable combination of the components (A), (B) and (C) comprises lauroyl-β-alanine potassium salt as (A), potassium laurate as (B) and laurylhydroxysulfobetaine as (C).

According to the present invention, a cleanser composition having the target properties can be obtained by using the components (A), (B) and (C) as defined above at a particular composition ratio.

That is to say, the cleanser composition of the present invention is characterized by containing the components (A), (B) and (C) at a mixing ratio by weight [(A+B)/C] of from 2.5/1 to 1/2, preferably from 2/1 to 1/2. As described above, the components (A) and (B) may be added in the form of a secondary amide-type N-acylamino acid or a higher fatty acid together with a base so as to form a secondary amide-type N-acylamino acid salt or a higher fatty acid salt in the formulation system. In such a case, the above-mentioned mixing ratio is calculated on the basis of the weight of each salt.

The contents of the components (A), (B) and (C) are not particularly restricted but selected within a range commonly employed in cleanser compositions. It is preferable that these components are each employed in an amount of from 0.1 to 5% by weight, still preferably from 0.5 to 4% by weight, based on the whole cleanser composition. A cleanser composition having particularly appropriate properties can be obtained by adjusting the total content of the components (A), (B) and (C) to 0.5 to 15% by weight.

In the present invention, the ratio of (A+B)/C is regulated from 2.5 to 0.5. Thus, it has been succeeded for the first time to obtain a cleanser composition which contains surfactants at such a regulated concentration as to give no irritation to the skin or mucosa, imparts an appropriate viscosity to the composition while using substantially no thickener and exhibits a high convenience in use and a good feel during and after cleansing, in addition to the fundamental characteristics as a cleanser (e.g., little irritation, excellent foaming power, sustained foaming, etc.).

The expression "using substantially no thickener" as used herein does not mean "containing entirely no thickening composition". Namely, it is not denied thereby to use thickener(s) in such a level that no undesirable effect is exhibited thereby. More particularly speaking, use of thickening components in an amount of not more than 2% by weight is not excluded from the scope of "substantial use". It is still preferable to use not more than 1.0% by weight of thickening components.

In the present invention, it is particularly preferable to use the components (A), (B) and (C) in a combination so as to give a cleanser composition having a viscosity of from 300 to 3,000 cps, since a cleanser composition having particularly appropriate properties can be thus obtained.

The cleanser composition of the present invention may arbitrarily contain other surfactants such as anionic surfactants (e.g., alkylsulfates, alkylsulfonates, polyoxyethylene alkylsulfates, alkylbenzenesulfonates, N-acylsarcosine salts, N-acyl-N-methyltaurine salts, α-olefinesulfonates, higher fatty acid ester sulfonates, alkyl ether acetates, polyoxyethylene alkyl ether acetates, etc.), and nonionic surfactants (e.g., fatty acid amides, polyoxyethylene alkyl ethers, sugar esters, sugar ethers, sugar amides, etc.), so long as the effects of the present invention are not deteriorated thereby.

Furthermore, the cleanser composition of the present invention may arbitrarily contain other components commonly employed in cleansers, so long as the effects of the present invention are not deteriorated thereby. Examples of such additives include humectants (e.g., propylene glycol, sorbitol, glycerol, etc.), viscosity regulating agents (e.g., carboxyvinyl polymer, methyl cellulose, ethanol, polyoxyethylene glycol distearate, etc.), pearling agents, perfumes, coloring matters (i.e., dyes), UV absorbers, antioxidants, bactericides, anti-inflammatory agents, preservatives, etc.

The cleanser composition of the present invention may be produced by a conventional method. It is usually in the form of a liquid product contained in a plastic bottle, etc. It is appropriately used in particular as a face cleanser, a body cleanser or a shampoo.

EXAMPLE

To further illustrate the present invention in greater detail, and not by way of limitation, the following Examples will be given.

Example 1

Cleanser compositions as specified in the following Table 1 were prepared and evaluated in foaming power, viscosity and easiness in taking out from bottle in accordance with the methods and evaluation as described hereinafter. The results are shown in Table 1.

(Determination of foaming power)

Each cleanser composition was diluted to 20-times with water. 100 ml of the solution thus obtained was poured into a 1,000 ml calibrated cylinder. Then stirring blades were located in the solution. After stirring for 30 seconds, the volume (ml) of the foam thus formed was measured to thereby evaluate the foaming power. The stirring blades were rotated at 1,000 rpm and reversed every 5 seconds.

Evaluation:

o: foam volume≧200 ml.

Δ: foam volume<200 ml.

(Determination of viscosity)

By using a Brookfield type viscometer, the viscosity was measured after stirring with the use of the rotor No. 3 at 30 rpm.

(Evaluation of easiness in taking out from bottle)

A polyethylene bottle provided with an inside stopper (pore diameter: 2 mm) and containing each cleanser composition was placed sideways and seized. Thus the easiness in taking out the cleanser composition from the bottle was evaluated according to the following evaluation.

o: the product can be taken out in a desired amount merely by lightly seizing.

Δ: the product is not viscous and thus flows out when placed sideways, thus being poor in convenience.

x: the product cannot be taken out until seizing tightly, thus being poor in convenience.

The easiness in taking out form bottle was evaluated by 5 female panelists and 5 male panelists. Almost all of these panelists almost agreed in evaluation.

TABLE 1

| Component | (expressed in wt. %) | | | | | |
|---|---|---|---|---|---|---|
| | (1) | (2) | (3) | (4) | (5) | (6) |
| (A) Lauroyl-β-alanine potassium | 2.4 | 4.8 | 1.2 | 0.6 | 0.1 | 1.2 |
| (B) Potassium laurate | 2.6 | 1.3 | 1.9 | 1.3 | 2.1 | 3.8 |
| (B) Potassium | 2.5 | 1.3 | 1.9 | 1.3 | 1.1 | — |

TABLE 1-continued

| Component | (expressed in wt. %) | | | | | |
|---|---|---|---|---|---|---|
| | (1) | (2) | (3) | (4) | (5) | (6) |
| myristate | | | | | | |
| (C) Lauroylhydroxy-sulfobetaine | 3.0 | 3.0 | 4.0 | 5.0 | 6.0 | 4.0 |
| Purified water | the balance | ← | ← | ← | ← | ← |
| (A + B)/C | 2.5 | 2.5 | 1.3 | 0.6 | 0.6 | 1.3 |
| Foaming power | o | o | o | o | o | o |
| Viscosity (CPS) | 2000 | 500 | 1000 | 1300 | 400 | 1500 |
| Easiness in taking | o | o | o | o | o | o |

COMPARATIVE EXAMPLE

For comparison, cleanser compositions listed in Table 2 were prepared by using the same components as those employed in Example 1 except that different mixing ratios (i.e., excluded from the range as specified in the present invention) were used. The properties of thus-obtained cleanser compositions were evaluated in the same manner as described in Example 1. The results are shown in Table 2 below.

TABLE 2

| Component | (expressed in wt. %) | | | | |
|---|---|---|---|---|---|
| | (7) | (8) | (9) | (10) | (11) |
| (A) Lauroyl-β-alanine potassium | 4.8 | 4.8 | 4.8 | 0.3 | 3.0 |
| (B) Potassium laurate | 3.8 | 1.3 | 2.6 | 1.9 | 0.0 |
| (B) Potassium myristate | 3.7 | 1.3 | 2.5 | 0.0 | 0.0 |
| (C) Lauroylhydroxy-sulfobetaine | 0.0 | 0.5 | 3.5 | 5.0 | 3.0 |
| Purified water | the balance | ← | ← | ← | ← |
| (A + B)/C | ∞ | 14.8 | 2.8 | 0.4 | 1.0 |
| Foaming power | o–Δ | Δ | o | Δ | Δ |
| Viscosity (CPS) | 160 | 170 | 5000 | 200 | 180 |
| Easiness in taking out from bottle | Δ | Δ | x | Δ | Δ | o–Δ means midle of o and Δ

Example 2

Liquid face cleansers of the compositions as specified in Table 3 were prepared and the properties thereof were determined and evaluated in the same manner as in Example 1. The results are shown in Table 3 below.

In this Example, lauroyl-β-alanine (i.e., a secondary amide-type N-acylamino acid) and lauric acid and myristic acid (i.e., fatty acids) were added respectively as the component (A) and the component (B) to thereby form potassium salts thereof in the formulation system together with potassium hydroxide added simultaneously.

The pH value of each sample was determined by preparing a 5% aqueous solution and measuring the pH value with a pH meter (DELTA 345; manufactured by METTLER) by the conventional method. The results are shown in Table 3 below.

TABLE 3

| Component | (12) | (13) | (14) |
|---|---|---|---|
| | (expressed in wt. %) | | |
| Hydroxyethyl cellulose hydroxy-propyltrimethylammonium chloride ether | 0.05 | 0.05 | 0.05 |
| 48% Potassium hydroxide | 2.50 | 2.50 | 2.50 |
| Lauryol-β-alanine | 1.00 | 3.80 | 3.80 |
| Lauric acid | 2.00 | 1.00 | 1.00 |
| Myristic acid | 2.00 | 1.00 | 1.00 |
| Laurylhydroxysulfobetaine | 3.30 | 3.30 | 4.00 |
| Polyoxyethylene sorbitan tristearate (160 E.O.) 86% Glycerol | 1.50 | 1.50 | 1.50 |
| | 10.00 | 10.00 | |
| Sorbitol | | | 10.00 |
| Ethylene glycol distearate | 2.00 | 2.00 | 2.00 |
| Dibutylhydroxytoluene | 0.10 | | 0.10 |
| Hydroxyethanediphosphonic acid | 0.10 | | |
| Ethyl parahydroxybenzoate | 0.20 | 0.20 | |
| Propyl parahydroxybenzoate | 0.10 | 0.10 | 0.10 |
| 55% Ethanol | 7.00 | 7.00 | 7.00 |
| Perfume | 0.07 | 0.10 | 0.15 |
| Purified water | the balance | ← | ← |
| pH | 8.82 | 7.95 | 8.91 |
| Foaming power | ⊚ | ⊚ | ⊚ |
| Viscosity (cps) | 500 | 700 | 1300 |
| Easiness in taking out from bottle | ⊚ | ⊚ | ⊚ |

In Example 2, regarding appearance, each of these face cleansers showed neither any separation out nor yellowing. It could be easily taken out in a desired amount merely by lightly seizing the bottle containing the same. When used for cleansing the face in practice, it was excellent in the foaming power and sustained foaming and exhibited a good feel in use without giving any squeak or stiff feel during and after use.

Therefore the preset invention provides a cleanser composition suitable particularly for liquid body cleansers which contains surfactants at such a regulated concentration as to give no irritation to the skin or mucosa, imparts an appropriate consistency to the cleanser without using any thickener and exhibits a high convenience in use and a good feel during and after cleansing, in addition to the fundamental characteristics as a cleanser (e.g., little irritation, excellent foaming power, sustained foaming, etc.). Thus, the present invention is highly useful in practice.

While the invention has been described in detail and with reference to specific embodiments thereof, it will be apparent to one skilled in the art that various changes and modifications can be made therein without departing from the spirit and scope thereof.

What is claimed is:

1. A cleanser composition comprising the following components (A), (B) and (C):

(A) an alkali metal salt of a secondary amide N-acylamino acid represented by formula (1):

$$R^1CONH(CH_2)_nCOOH \tag{1}$$

wherein $R^1CO$ represents a linear acyl group having 10 to 16 carbon atoms; and n is a number of 1 or 2;

(B) an alkali metal salt of a higher fatty acid; and (C) an amphoteric surfactant;

wherein the mixing ratio by weight of (A+B)/C ranges from 2.5/1 to 1/2 and wherein the contents of said components (A), (B) and (C) each range from 0.1 to 5% by weight of the cleanser composition.

2. A cleanser composition as claimed in claim 1, wherein the total content of said components (A), (B) and (C) ranges from 0.5 to 15% by weight of the cleanser composition.

3. A cleanser composition as claimed in claim 1, wherein the viscosity of the cleanser composition ranges from 300 to 3,000 cps.

4. A cleanser composition as claimed in claim 1, wherein said component (C) is hydroxysulfobetaine.

5. A cleanser composition as claimed in claim 1 which is substantially free from any thickening component.

6. A cleanser composition as claimed in claim 1 which contains from 0.1 to 2.0% by weight of a thickening component.

* * * * *